United States Patent [19]

Haas et al.

[11] Patent Number: 5,364,987
[45] Date of Patent: Nov. 15, 1994

[54] PROCESS FOR THE PREPARATION OF 1,3-PROPANEDIOL

[75] Inventors: Thomas Haas, Frankfurt am Main; Dietrich Arntz, Oberursel, both of Germany

[73] Assignee: Degussa Aktiengesellschaft, Frankfurt, Germany

[21] Appl. No.: 86,040

[22] Filed: Jul. 6, 1993

[30] Foreign Application Priority Data

Jul. 10, 1992 [DE] Germany ............................. 4222708

[51] Int. Cl.$^5$ ...................... C07C 31/20; C07C 29/141
[52] U.S. Cl. ..................................... 568/866; 568/862; 568/865
[58] Field of Search .................... 568/862, 868, 865; 566/866

[56] References Cited

U.S. PATENT DOCUMENTS

| | | | |
|---|---|---|---|
| 4,254,290 | 3/1981 | Chambers et al. | 568/866 |
| 4,806,658 | 2/1989 | Chang et al. | |
| 5,015,789 | 5/1991 | Arntz et al. | |
| 5,093,537 | 3/1992 | Unruh et al. | |
| 5,171,898 | 12/1992 | Arntz et al. | |

FOREIGN PATENT DOCUMENTS

| | | |
|---|---|---|
| 898894 | 12/1953 | Germany . |
| 3926136 | 8/1989 | Germany . |
| 4038192 | 11/1990 | Germany . |

*Primary Examiner*—Johann Richter
*Assistant Examiner*—Rebecca Cook
*Attorney, Agent, or Firm*—Beveridge, DeGrandi, Weilacher & Young

[57] ABSTRACT 1,3-propanediol (PD) is obtained by hydration of acrolein to 3-hydroxypropionaldehyde (HPA) with subsequent catalytic hydrogenation; 3,3'-oxybis-1-propanol (OD) occurs as a yield-reducing by-product. Disclosed is a process which increases the 1,3-propanediol yield. The OD which is separated by distillation during treatment of the reaction mixture containing PD and OD is treated in aqueous solution at from 100 to 300° C. with an acid solid catalyst, in particular an acid zeolite, and the reaction mixture from which the solid catalyst has been removed is returned into the treatment stage of the reaction mixture containing PD and OD.

13 Claims, 1 Drawing Sheet

PROCESS FOR THE PREPARATION OF 1,3-PROPANEDIOL

BACKGROUND AND INTRODUCTION

The present invention relates to a process for the preparation of 1,3-propanediol (PD) based on hydration of acrolein to 3-hydroxypropionaldehyde (HPA) with subsequent catalytic hydrogenation. According to the present invention, 1,3-propanediol is also obtained from the 3,3'-oxybis-1-propanol (OD) which arises as a by-product of this process.

1,3-propanediol has a wide variety of potential applications as a monomer structural unit for polyesters and polyurethanes and as a starting material in cyclic compound synthesis.

Various processes are known for the preparation of 1,3-propanediol, and these either take as their starting point a molecular structure from a $C_2$ and $C_1$ structural unit or, preferably, start directly from a $C_3$ structural unit (e.g., acrolein). The processes for the preparation of 1,3-propanediol which take acrolein as their starting point are based on two reaction stages: (a) hydration of acrolein in the presence of an acid hydration catalyst and (b) catalytic hydrogenation of the reaction mixture from stage (a) which contains 3-hydroxypropionaldehyde and from which unreacted acrolein has been removed. The reaction mixture of stage (b) contains 3,3'-oxybis-1-propanol (Chem. Abstr. Registry No. 2396-61-4; also known as 4-oxa-1,7-heptanediol or bis(3-hydroxypropyl)ether) in addition to 1,3-propanediol, water and by-products which boil above the boiling point of 1,3-propanediol. The reaction mixture of stage (b) is treated by distillation to yield pure 1,3-propanediol.

The equations for stages (a) and (b) are as follows:

(a) 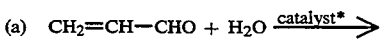

$$HOCH_2-CH_2-CHO$$

*acid hydration catalyst (b) 

$$HOCH_2-CH_2-CH_2OH$$

**hydrogenation catalyst

As disclosed by U.S. Pat. No. 2,434,110 (incorporated by reference), hydration can be performed at a raised temperature with use of from 5 to 30 wt % solution of acrolein in water in the presence of an acid (e.g., sulphuric acid, phosphoric acid or acid salts of these acids) with 3-hydroxypropionaldehyde being produced. Hydrogenation of the reaction mixture from which unreacted acrolein has been removed can be performed over conventional hydrogenation catalysts containing one or more metals which can bring about hydrogenation, for example Fe, Co, Ni, Cu, Ag, Mo, W, V, Cr, Rh, Pd, Os, Ir, or Pt. The selectivity of the hydration stage has a decisive influence on the 1,3-propanediol yield. Various catalyst systems have therefore been proposed in order to enable hydration with high selectivity to be carried out in a simple manner on an industrial scale. Examples of hydration catalysts which have been proposed include the following: cation exchange resins having phosphonic acid groups (DE-OS 39 26 136; U.S. Pat. No. 5,015,789, incorporated by reference); chelate-forming ion exchangers such as those having methyleneiminodiacetic acid anchoring groups (DE-OS 40 38 192; U.S. Pat. No. 5,171,898, incorporated by reference); acid-base buffers of organic carboxylic acids or phosphoric acid and salts of these acids which result in a reaction mixture pH of from 2 to 5 (DE Application P 41 38 981.6; U.S. patent application Ser. No. 07/980,955 filed on Nov. 24, 1992, now U.S. Pat. No. 5,284,979, is incorporated by reference)); and inorganic support media having basic activity centers, some of which are occupied by a monovalent acid in a form in which it cannot be detached by water (DE Application P 41 38 982.4; U.S. patent application Ser. No. 07/981,324 filed on Nov. 24, 1992, now U.S. Pat. No. 5,276,201, is incorporated by reference))). A mixture of acrolein and water in a weight ratio of from 1 to 2 to 1 to 20 is normally utilized for the hydration and the reaction is carried out either batchwise or continuously at from 30° to 120° C. at a pressure within the range 1 to 20 bar.

Catalytic hydrogenation of the reaction mixture from the hydration stage from which the acrolein has been removed is generally conducted at a pH within the range 2.5 to 6 and at a temperature within the range 30° to 180° C. Hydrogenation is expediently conducted at from 30° to 80° C. until conversion within the range 50 to 95% is achieved, with further hydrogenation to 100% conversion being conducted at from 100° to 180° C. According to the process of German Patent Application 41 32 663.5 (corresponding to U.S. patent application Ser. No. 07/948,718 filed on Sep. 24, 1992, pending, is incorporated by reference), supported catalysts of titanium dioxide on which platinum is present in a finely-divided form are particularly good hydrogenation catalysts, enabling both a high degree of conversion and also high selectivity to be achieved.

A substantial disadvantage of all the processes disclosed hitherto for the preparation of 1,3-propanediol by acrolein hydration and catalytic hydrogenation of 3-hydroxypropionaldehyde (HPA) lies in the fact that various side-reactions, in particular during the hydration stage, diminish the total 1,3-propanediol yield. 3,3'-oxybis-1-propanol and 4-hydroxy-3-hydroxymethyltetrahydropyrane were the principal products detected in the high boiling point fraction (boiling point above that of 1,3-propanediol) during treatment of the reaction mixture from catalytic hydrogenation.

SUMMARY OF THE INVENTION

An object of the present invention is to provide an efficient process for increasing the 1,3-propanediol yield in a process for the preparation of 1,3-propanediol from acrolein and a way of reducing the proportion of high boiling point by-products which must be removed.

In achieving the above and other objects, one feature of the present invention resides in a process for the preparation of 1,3-propanediol which includes the following stages:
(a) hydration of acrolein in the presence of an acid hydration catalyst,
(b) catalytic hydrogenation of the reaction mixture from stage (a) which contains 3-hydroxypropionaldehyde and from which unreacted acrolein has been removed, and
(c) treating, by distillation, the reaction mixture from stage (b) which contains water, 1,3-propanediol and by-products having boiling points higher than that of 1,3-propanediol, wherein 3,3′-oxybis-1-propanol is separated by distillation from the by-products having boiling points higher than that of 1,3-propanediol, the 3,3′-oxybis-1-propanol is treated in aqueous solution at from 100° to 300° C. with an acid solid catalyst in order to cleave the ether 3,3′-oxybis-1-propanol, and the reaction mixture from which the solid catalyst has been removed is returned to stage (c).

Another feature resides in acid solid catalysts which can be utilized for the ether cleaving of the process according to the present invention; such catalyst include, for example, gamma-aluminum oxide, acid ion exchangers, natural and synthetic zeolites and inorganic supports occupied with acids in a form in which they cannot be detached by water (e.g., titanium dioxide treated with phosphoric acid and then calcined. Acid zeolites having a Si/Al atomic ratio of more than 2 to about 100, especially more than 10 to 40, are preferred as solid catalyst because of the very wide range of conversions and selectivities obtainable with the various acid solid catalysts. Zeolites of the ZSM5 type are particularly suitable while dealuminised zeolites of the Y type are less preferred than ZSM5 zeolites.

BRIEF DESCRIPTION OF THE DRAWING

The present invention will be further understood from a study of the drawing, wherein.

DETAILED DESCRIPTION OF THE INVENTION

Figure 1:
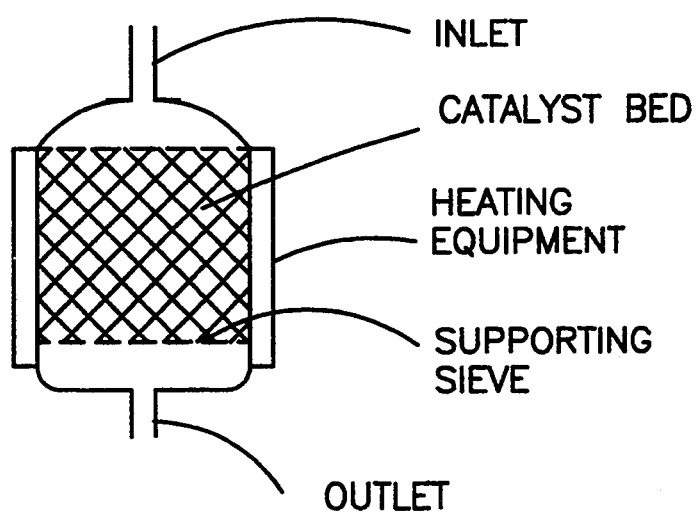
FIG. 1 shows a fixed bed reactor in which 3,3′-oxybis-1-propanol can be cleaved continuously by feeding an aqueous solution of 3,3′-oxybis-1-propanol over acid solid catalyst disposed in the fixed bed reactor.

Stages (a) and (b) which were previously known, that is to say the hydration and the catalytic hydrogenation, are conducted in a manner which is known to those skilled in the art, for example by a process of the documents incorporated by reference above. It is essential to the present invention that in step (c), when treating the reaction mixture from the hydrogenation stage by distillation, that not only are water and then 1,3-propanediol distilled off, but 3,3′-oxybis-1-propanol is also distilled off from the high boiling point fraction and is then fed to the ether cleaving step. Where the entire high boiling point fraction is subjected to cleaving of the ether, there will also occur those by-products (including 3-hydroxymethyl-tetrahydropyrane) which impede obtaining pure 1,3-propanediol if the entire reaction mixture from the ether cleaving step is returned to the distilling treatment stage (c) because of the similarity of boiling points.

3,3′-oxybis-1-propanol can per se be cracked to form 1,3-propanediol in a manner which is known per se in an aqueous solution in the presence of mineral acids (i.e., liquid catalysts). However, such a measure is not efficient because the reaction mixture from ether cleaving cannot be returned into the distilling treatment stage (c). In the event of separate treatment of the reaction mixture from ether cleaving using mineral acids, however, a large amount of effluent is produced.

In the process of the present invention, the use of acid solid catalysts in order to cleave the ether 3,3′-oxybis-1-propanol enables the reaction mixture from which the solid catalyst has been removed to be returned into the distilling treatment stage without any further treatment measure. This is a substantial advantage of the process according to the present invention. 3,3′-oxybis-1-propanol thus produces 3-propanediol:

$$(HO-CH_2-CH_2-CH_2)_2O + H_2O \rightarrow 2\ HO-CH_2-CH_2-CH_2-OH$$

Different acid solid catalysts can be utilized for the ether cleaving of the process according to the present invention; such catalyst include, for example, gamma-aluminum oxide, acid ion exchangers, natural and synthetic zeolites and inorganic supports occupied with acids in a form in which they cannot be detached by water (e.g., titanium dioxide treated with phosphoric acid and then calcined (DE Application P 41 38 982.4; U.S. patent application Ser. No. 07/981,324 filed on Nov. 24, 1992, now U.S. Pat. No. 5,276,201, is incorporated by reference)). Acid zeolites having a Si/Al atomic ratio of more than 2 to about 100, especially more than 10 to 40, are preferred as solid catalyst because of the very wide range of conversions and selectivities obtainable with the various acid solid catalysts. Zeolites of the ZSM5 type which are known in the art are particularly suitable. Dealuminized zeolites of the Y type also catalyze ether cleaving, but present-day knowledge suggests that they exhibit a lower long-term stability than ZSM5 zeolites.

Although the cleaving of the ether 3,3′-oxybis-1-propanol according to the present invention is possible in diluted or concentrated aqueous solution, solutions having a 3,3′-oxybis-1propanol content of between 5 and 40 wt %, in particular between 10 and 30 wt %, are preferably utilized. The reaction temperature influences conversion and selectivity of the ether cleaving. The ether is preferably cleaved within the temperature range 150° to 250° C. In order to avoid water loss during cleaving of the ether, one generally works in a sealed apparatus at the pressure resulting from the reaction temperature or at a higher pressure.

The cleaving of the ether which characterizes the process according to the present invention can be performed either batchwise or continuously in conventional reactors suitable for reactions in the presence of solid catalysts. It is particularly expedient to dispose the solid catalyst in a fixed bed reactor (see FIG. 1) and to feed the aqueous 3,3′-oxybis-1-propanol solution over the fixed bed at a required reaction temperature at a LHSV (liquid hourly spatial velocity) such that the desired conversion is obtained. As is apparent from the Examples below, conversions and selectivities within the range 60 to about 75% can be achieved without difficulty. The process according to the present invention consequently enables a large proportion of the 3,3′-oxybis-1-propanol which is formed as a by-product during hydration and subsequent catalytic hydrogenation to be converted in a simple manner to 1,3-propanediol; the occurrence of high boiling point by-products which must be removed is reduced by a proportion which corresponds to the increase in yield.

EXAMPLES 1 to 6

In order to determine the effectiveness of fixed bed catalysts for cleaving the ether 3,3′-oxybis-1-propanol (OD), a 10 ml steel flask is in each case charged with 7 ml catalyst and sufficient water is added to just cover the catalyst. OD is additionally added to adjust the OD concentration in the aqueous phase to the desired level. The sample is shaken for a predetermined reaction time in a hot air oven at the temperature indicated. The sample is then quenched in a water jet and analyzed; see the following table.

| Example No. | Catalyst | $T_R$ (°C.) | t (h) | $C_{OD,E}$ (wt %) | $C_{OD,P}$ (wt %) | $C_{PD,P}$ (wt %) | U (%) | S (%) |
| --- | --- | --- | --- | --- | --- | --- | --- | --- |
| 1 | Amberlyst (type: . . . ) | 150 | 2 | 20.00 | 18.06 | 1.26 | 9.70 | 57 |
| 2 | Mordenit | 250 | 2 | 7.63 | 6.71 | 0.76 | 12.10 | 73 |
| 3 | Mordenit | 250 | 2 | 20.00 | 16.73 | 1.66 | 16.40 | 45 |
| 4 | gamma-Al$_2$O$_3$ | 250 | 2 | 7.63 | 7.06 | 0.39 | 7.50 | 60 |
| 5 | dealuminised Y zeolite (Si/Al atomic ratio = ca. 100) | 250 | 2 | 20.00 | 5.32 | 12.02 | 73.40 | 72 |
| 6 | zeolite ZSM5 (Si/Al atomic ratio = 14) | 180 | 2 | 20.00 | 4.80 | 10.34 | 76.00 | 60 |

(C = concentration; OD = 3,3'-oxybis-1-propanol; PD = 1,3-propanediol, index E or P = substance utilized or product; U = conversion; S = selectivity).

EXAMPLE 7

Continuous OD hydrolysis is carried out for a protracted period in a laboratory apparatus having a fixed bed reactor with a ZSM5 zeolite (Si/Al=14) catalyst. Conversion and selectivity are determined by analysis of the product solution. The apparatus comprises a receiver for the OD solution, an HPLC conveying pump, a hot air oven in which a preheating stretch and the reaction tube (160×15 mm internal diameter) are installed. Downstream of the reactor the liquid is cooled to room temperature. The entire apparatus is maintained at a pressure of 50 bar in order to prevent water evaporation. The product solution is analyzed at regular intervals.

OD starting concentration: 20 wt %
Reaction temperature: 2400°-250° C.
Reaction pressure: 50 bar
LHSV: 0.5/h The total duration of the experiment was 300 h. Conversion was 60±5%. The temperature was increased from 240° C. to 250° C. during the course of the experiment in order to keep conversion constant. Reaction selectivity was 70±3%.

EXAMPLE 8

Complete Process With and Without Oxdiol Hydrolysis 2 kg H$_2$O were mixed with 400 g acrolein. The acrolein hydration was then carried out in a reaction tube charged with the ion exchanger Lewatit TP 208 (H form). Reaction temperature=45° C.; LHSV=0.5/h. The unreacted acrolein was then separated from the aqueous HPA solution at reduced pressure (350 mbar).

The acrolein conversion was 51%, the selectivity vis-à-vis HPA was 85% (HPA concentration=10.4% after separation of acrolein).

The HPA solution was hydrogenated in a hydrogenation autoclave with a gas stirrer. The H$_2$ pressure was 135 bar and the reaction temperature 60° C.; 20 g Raney nickel was utilized as catalyst. The 1,3-propanediol (PD) yield, calculated on 3-hydroxypropionaldehyde (HPA) utilized, was 99.8%.

2200 g of the aqueous PD solution obtained was divided into two equal portions. Water was distilled off in a distillation column from the first half at 50 mbar. 134.1 g PD and high boiling point fractions remained in the sump. After increasing the sump temperature to 134° C., 115.1 g of PD was distilled off. The PD yield over all stages was thus 83%. 18.7 g of high boiling point fractions remained in the sump. 13.1 g OD was distilled off from the sump at 20 mbar and 155° C.; this 13.1 g was diluted with 52.4 g H$_2$O and reacted on a ZSM5 zeolite as in Example 7. The product solution contained 6.2% unreacted OD and 9.6% PD. This solution was combined with the second half of the hydrogenation solution. 120.4 g PD and 16.5 g OD were distilled off after separation of the H$_2$O.

4.6% more PD was therefore isolated than in the experiment without OD hydrolysis. Since the unreacted OD fraction (3.4 g) is recycled in a continuous operation and is reacted with a selectivity of approximately 70%, the PD yield is increased by a further 2.4%, thus giving a 7% total increase in yield.

Further variations and modifications of the foregoing will be apparent to those skilled in the art and such variations and modifications are attended to be encompassed by the claims that are appended hereto.

U.S. patent application Ser. No. 08/063,317 filed on May 19, 1993, now abandoned, is incorporated by reference (corresponding to German Patent Application 42 18 282.4).

What is claimed:

1. A process for the preparation of 1,3-propanediol, said process comprising
   (a) hydrating acrolein in the presence of a hydration catalyst,
   (b) catalytically hydrogenating the reaction mixture from (a) which contains 3-hydroxypropionaldehyde and from which unreacted acrolein has been removed,
   (c) distilling the reaction mixture from (b) which contains water, 1,3-propanediol and by-products having boiling points higher than that of 1,3-propanediol; separating 3,3'-oxybis-1-propanol from the by-products having boiling points higher than that of 1,3-propanediol and treating said 3,3'-oxybis-1-propanol in aqueous solution at from 100° to 300° C. with an acid solid catalyst in order to cleave 3,3'-oxybis-1-propanol to form 1,3-propanediol, and the resulting reaction mixture from which the solid catalyst has been removed is returned to (c).

2. The process according to claim 1, wherein said 3,3'-oxybis-1-propanol treated by said acid solid catalyst is in the form of a 5 to 40 wt % aqueous solution.

3. The process according to claim 2, wherein said 3,3'-oxybis-1-propanol is in the form of a 10 to 30 wt % aqueous solution.

4. The process according to claim 1, wherein said acid solid catalyst is an acid zeolite.

5. The process according to claim 4, wherein said acid zeolite has a Si/Al atomic ratio greater than from 2 to approximately 100.

6. The process according to claim 5, wherein said acid zeolite has a Si/Al atomic ratio greater than from 10 to approximately 40.

7. The process according to claim 4, wherein said acid zeolite is a ZSM5 zeolite.

8. The process according to claim 1, wherein said 3,3'-oxybis-1-propanol in aqueous solution is treated from 150° to 250° C.

9. The process according to claim 1, wherein said 3,3'-oxybis-1-propanol is cleaved continuously by feeding said aqueous solution of 3,3'-oxybis-1-propanol over said acid solid catalyst disposed in a fixed bed reactor.

10. The process according to claim 1, wherein in step (c) water, 1,3-propanediol, and 3,3'-oxybis-1-propanol is distilled off from the by-products having high boiling points higher than that of 1,3-propandiol.

11. The process according to claim 1, wherein said acid solid catalyst is selected from the group consisting of gamma-aluminum oxide, acid ion exchangers, natural and synthetic zeolites and inorganic supports occupied with acids in a form in which they cannot be detached by water.

12. The process according to claim 11, wherein said acid solid catalyst is titanium dioxide treated with phosphoric acid and then calcined.

13. A process for the preparation of 1,3-propanediol, said process consisting essentially of
  (a) hydrating acrolein in the presence of a hydration catalyst,
  (b) catalytically hydrogenating the reaction mixture from (a) which contains 3-hydroxypropionaldehyde and from which unreacted acrolein has been removed,
  (c) distilling the reaction mixture from (b) which contains water, 1,3-propanediol and by-products having boiling points higher than that of 1,3-propanediol; separating 3,3'-oxybis-1-propanol from the by-products having boiling points higher than that of 1,3-propanediol and treating said 3,3'-oxybis-1-propanol in aqueous solution at from 100° to 300° C. with an acid solid catalyst in order to cleave 3,3'-oxybis-1-propanol to form 1,3-propanediol, and the resulting reaction mixture from which the solid catalyst has been removed is returned to (c).

* * * * *